(12) United States Patent
Asher et al.

(10) Patent No.: US 9,304,074 B2
(45) Date of Patent: Apr. 5, 2016

(54) METHODS FOR MAKING AND COMPOSITIONS OF TWO DIMENSIONAL PARTICLE ARRAYS

(75) Inventors: Sanford A. Asher, Pittsburgh, PA (US); Alexander Tilchonov, Pittsburgh, PA (US); Luling Wang, Mesa, AZ (US); Jian-Tao Zhang, Pittsburgh, PA (US)

(73) Assignee: University of Pittsburgh—Of The Commonwealth System of Higher Education, Pittsburgh, PA (US)

( * ) Notice: Subject to any disclaimer, the term of this patent is extended or adjusted under 35 U.S.C. 154(b) by 558 days.

(21) Appl. No.: 13/553,555

(22) Filed: Jul. 19, 2012

(65) Prior Publication Data

US 2014/0204364 A1    Jul. 24, 2014

Related U.S. Application Data

(60) Provisional application No. 61/509,284, filed on Jul. 19, 2011.

(51) Int. Cl.
*G01N 15/02*  (2006.01)
*G01N 21/01*  (2006.01)
*G01N 21/47*  (2006.01)

(52) U.S. Cl.
CPC ............ *G01N 21/01* (2013.01); *G01N 21/4788* (2013.01)

(58) Field of Classification Search
CPC ........................................................ G01N 15/02
USPC .......................................................... 356/336
See application file for complete search history.

(56) References Cited

U.S. PATENT DOCUMENTS

| | | | |
|---|---|---|---|
| 7,396,569 B2* | 7/2008 | Lalli et al. ...................... | 427/409 |
| 8,309,185 B2* | 11/2012 | Lin et al. ........................ | 427/569 |
| 2004/0005723 A1* | 1/2004 | Empedocles et al. ............. | 438/1 |
| 2005/0064204 A1* | 3/2005 | Lalli et al. ...................... | 428/428 |
| 2006/0235086 A1* | 10/2006 | Maskaly et al. ................ | 516/77 |
| 2007/0125181 A1* | 6/2007 | Ofek et al. ...................... | 73/778 |
| 2008/0017845 A1* | 1/2008 | Drndic et al. ................... | 257/24 |

* cited by examiner

*Primary Examiner* — Roy M Punnoose
(74) *Attorney, Agent, or Firm* — Paul D. Bangor, Jr.; Clark Hill, PLC

(57) ABSTRACT

A method of preparation of a 2-D array of particles comprising: mixing the particles and a first liquid, the first liquid having the properties of being soluble in water and reducing surface tension of a water surface; adding the mixture to the water surface; and transferring the 2-D array onto a solid surface. A composition comprising: a 2-D array of particles; and a polymer substantially enveloping the 2-D array of particles.

7 Claims, 12 Drawing Sheets

METHODS FOR MAKING AND COMPOSITIONS OF TWO DIMENSIONAL PARTICLE ARRAYS

CROSS REFERENCE TO RELATED APPLICATIONS

This application claims the benefit of provisional patent application U.S. Ser. No. 61/509,284, filed Jul. 19, 2011, by the present inventors, and is incorporated by reference herein for all purposes.

STATEMENT REGARDING FEDERALLY SPONSORED RESEARCH OR DEVELOPMENT

This invention was made with United States government support under grant number HDRA 1-10-1-0044 awarded by the Department of Defense. The government has certain rights in the invention.

TECHNICAL FIELD OF INVENTION

The field of endeavor to which the invention generally relates is field of two-dimensional (2-D) films and more specifically to two-dimensional particle arrays and methods for fabricating and using 2-D particle arrays having high diffraction efficiency for molecular recognition and chemical sensing applications. Photonic crystals (PC) are of great interest owing to their potential applications in areas such as chemical sensing, colloidal lithography and waveguiding. The 2-D array PC behaves similarly to a 2-D diffraction grating that diffracts light into various Bragg diffraction orders. The diffracted beams either propagate outside the 2-D array PC or propagate within the 2-D array PC in guided modes.

BACKGROUND

It is essential to identify and quantitate hazardous physical, chemical or biological agents remotely before they achieve dangerous levels. The ideal sensing technology should be able to separately and selectively detect the largest subset of chemical and biological agents with high sensitivity. This has motivated the development of numerous sensing approaches. Many of these approaches rely on sophisticated analytical techniques such as mass spectrometry, fluorescence, Raman spectroscopy, etc., that have disadvantages of complexity and cost.

Improved approaches to chemical sensing preferably would use methods that do not require sample preparation and that allow the visual determination of the chemical species and their concentrations. In one example of such an approach, three-dimensional (3-D) polymerized colloidal crystal array (PCCA) hydrogel sensing materials used diffraction to measure analyte. These 3-D photonic crystal materials were fabricated through self assembly of face center cubic (FCC) arrays of colloidal particles followed by polymerization to embed the colloidal crystal array (CCA) within a hydrogel network. The PCCA was then functionalized with the appropriate molecular recognition agents. These sensing materials detect analytes such as creatinine, glucose, pH, organophosphorus compounds, amino acids and metal ions.

Diffraction is typically relatively weak for 2-D particle arrays, e.g. polystyrene particles in air back diffract 1-10% of the incident light, depending on the colloidal particle diameter. The diffraction efficiency generally increases with the magnitude of the 2-D particle arrays dielectric constant modulation. Very large diffraction efficiencies can be achieved from metallic 2-D particle arrays or if multiple dielectric 2-D particle layers are stacked to form a 3-D particle arrays.

BRIEF SUMMARY OF THE INVENTION

Maximizing diffraction efficiencies from a two dimensional (2-D) particle array is the basis of the present disclosure. A preferred embodiment of the present disclosure is the first development of high diffraction efficiency 2-D photonic crystals for molecular recognition and chemical sensing applications. This development is a facile approach to fabricating close packed 2-D colloidal particle arrays by solvent evaporation of an assembling monolayer on a mercury surface. The 2-D particle array diffracts 80% of incident light. Then the 2-D array was transferred onto a hydrogel thin film that shows a hydrogel volume phase transition in response to environmental stimuli. This altered the array spacing, shifting the 2-D array diffraction wavelength. These 2-D array photonic crystals exhibit ultra-high diffraction efficiencies that enable them to be used for visually attractive paints and coatings and visual determination of analyte concentrations.

It is to be understood that the descriptions of the present disclosure have been simplified to illustrate elements that are relevant for a clear understanding of the present disclosure, while eliminating, for purposes of clarity, other elements that may be well known. Those of ordinary skill in the art will recognize that other elements are desirable and/or required in order to implement the present disclosure. However, because such elements are well known in the art, and because they do not facilitate a better understanding of the present disclosure, a discussion of such elements is not provided herein. Additionally, it is to be understood that the present disclosure is not limited to the embodiments described above, but encompasses any and all embodiments within the scope of the description and the following claims.

In a first preferred aspect of the invention, a 2-D array of particles is prepared by the steps comprising mixing the particles in a first liquid, the first liquid having the properties of being soluble in water and reducing the surface tension of a water surface, adding the mixture onto water or mercury, and transferring the 2-D array onto a solid surface. In preferred embodiments, the 2-D array is close packed. In other preferred embodiments, the first liquid is miscible with water. In a preferred embodiment, the mixture is added to the surface of the water. In preferred embodiments, the solid surface is reflective. In various embodiments, the solid surface may be planar, curved, angled, smooth, or rough. In other preferred embodiments, the solid surface may be of any article of manufacture. In preferred embodiments, the solid surface is transparent. In additional preferred embodiments, the transparent solid surface is a glass or plastic. In further preferred embodiments, the reflective surface is a mirrored glass. In still other preferred embodiments, the reflective surface is a metal. In additional preferred embodiments, the metal surface is gold, silver, aluminum, copper, iron, steel, or reflective alloy. In preferred embodiments, the transfer occurs by bringing the solid surface in contact with the 2-D array on a side of the 2-D array away from the water phase or mercury surface. In other preferred embodiments, the transfer occurs by bringing the solid surface in contact with the 2-D array on the side of the water phase. In preferred embodiments, the transfer occurs by moving the 2-D array relative to the solid surface by the addition or removal of water, where removal of water may be by any means, for example by evaporation, draining, drawing off, absorption or other methods. In still other preferred embodiments, the 2-D array can be formed in a continuous manner by addition of the mixture to water where the water is moving relative to the point of introduction of the mixture.

In a second preferred aspect of the invention, the method of preparation of an embedded 2-D array comprises the steps of forming a 2-D array from particles, placing a polymer precursor solution onto the 2-D array, and polymerization of the polymer precursor solution to form the embedded 2-D array. In preferred embodiments, the 2-D array is close packed. In some preferred embodiments, the 2-D array is formed on the surface of a dense liquid. In other preferred embodiments, the dense liquid is mercury. In additional preferred embodiments, the method further comprises the step of placing an inert surface over the polymer precursor solution prior to polymerization. In preferred embodiments, the method further comprises the step of removing the embedded 2-D array from the inert surface. In preferred embodiments, the 2-D array is fully embedded in the polymer. In other preferred embodiments, the 2-D array is substantially embedded, wherein the particles of the 2-D array are not fully embedded in the polymer.

A third preferred aspect of the invention, the method of using the 2-D array of particles comprises the steps of transmitting light through a first side of the 2-D array of particles, transmitting light through a second side of the 2-D array of particles, and observing diffraction of the light. In various preferred embodiments, the solid surface may comprise any article of manufacture. In other preferred embodiments, the solid surface is reflective. In other preferred embodiments, the reflective surface is a mirrored glass. In yet other preferred embodiments, the reflective surface is a reflective plastic. In preferred embodiments having a reflective surface of mirrored glass or reflective plastic, the reflective surface may be of a single component or a laminate. In still other preferred embodiments, the reflective surface is a metal. In still additional preferred embodiments, the metal surface is gold, silver, aluminum, copper, iron, steel, or reflective alloy.

A fourth preferred aspect of the invention is a 2-D array of particle combination comprising a 2-D array of particles, and a solid reflective surface parallel to the 2-D array. In some preferred embodiments, the 2-D array combination is made from an array produced according to the first preferred aspect of the invention as described herein above. In other preferred embodiments, the 2-D array combination is made from an array produced of the second preferred aspect of the present invention as described herein above.

A fifth preferred aspect of the invention is a 2-D array of particle combination comprising a 2-D array of particles, and a hydrogel polymer substantially enveloping the 2-D array. In preferred embodiments, the combination further comprises a solid reflective surface parallel to the 2-D array of particles. In other preferred embodiments, the polymer is affixed to the solid reflective surface. In preferred embodiments the polymer is a hydrogel polymer. In still other preferred embodiments, the 2-D array hydrogel is affixed by a second polymerization with components on a face of the solid reflective surface. In additional preferred embodiments, the second polymerization has less cross-linking than in the polymer. In still other preferred embodiments, the second polymerization has longer polymer lengths than found in the polymer. In additional preferred embodiments, the spacing of the 2-D array may be expanded such that the embedded or substantially embedded 2-D array of particles is no longer close packed. In even further preferred embodiments, the surface area of the polymer may be expanded such that the embedded or substantially embedded 2-D array of particles is no longer close packed, and then restrained from reforming a close packing of particles, e.g. by physical means such as drying, stretching of the polymer, or by physical or chemical means by the affixing to an article of manufacture.

A sixth preferred aspect of the invention is a product affixed to an article of manufacture wherein the product is a chemical sensor wherein the 2-D array incorporates a polymer which has a 2-D area alterable by an external stimulus. In still other preferred embodiments, the product comprises the 2-D array as an anti-counterfeiting film affixed to an article of manufacture. In various preferred embodiments of the product aspects, the 2-D array is directly affixed to the article of manufacture such as currency bills. In other preferred embodiments, the 2-D array is embedded or substantially embedded in a polymer and the resultant array is affixed to the article of manufacture. In still other preferred embodiments, the 2-D array is affixed to a reflective surface or laminate including a reflective surface, and this is affixed to the article of manufacture. In still other preferred embodiments, the 2-D array is embedded or substantially embedded in a polymer and the 2-D array is affixed to a reflective surface, and the reflective surface is affixed to the article of manufacture.

In further preferred embodiments of the product as a sensor, the polymer would be responsive to change in pH by incorporation of carboxyl groups. Additional preferred embodiments are possible for compounds such as urea, uric acid, antigens, and antibodies; cations such as, but not limited to, sodium, potassium, calcium, magnesium, mercury, and ammonia; and for anions such as, but not limited to, chloride, carbonate, bicarbonate, and phosphate. Preferred embodiments of chemical sensors of the invention comprise cations and anions and may incorporate chelating agents into the polymer, where the chelating agents may include crown ethers, azacrown ethers, borane complexes, calixarene, and cation selective binding proteins. In preferred embodiments of the present invention as a sensor, the detection of the chemical will be by a visual change to the sensor due to a change in the surface area of the 2-D array embedded or substantially embedded in the polymer.

In some preferred embodiments of the various aspects comprising a polymer, the polymer is a non-ionic polymer. In some preferred embodiments, the polymer is a hydrogel. In other more preferred embodiments, the polymer comprises of a polymer having an acrylamide repeat unit. In preferred embodiments, the polymer comprises a crown ether. In other preferred embodiments, the polymer comprises hydroxyethyl methacrylate, N-isopropylacrylamide, and/or a crown ether acrylate. In still other preferred embodiments, the polymer incorporates ionic polymers. In some preferred embodiments, the ionic polymers comprise carboxylates or an acrylic acid repeat unit.

In some preferred embodiments of the 2-D arrays of the present invention, the particles are polystyrene. In other preferred embodiments, the particles are silica. In still other preferred embodiments, the particles are metal. In some preferred embodiments, the metal particles may comprise gold or silver. In still other preferred embodiments, the particles range from 100 nm to 2 micron in diameter. In various preferred embodiments, the 2-D arrays are close packed. In some preferred embodiments of the various aspects using a first liquid, the first liquid is miscible with water. In additional preferred embodiments, the liquid is an alcohol. In still further preferred embodiments, the alcohol is n-propyl alcohol. In preferred embodiments, the volume ratio of particles to first liquid is between 10:1 to 1:100. In additional preferred embodiments, the volume ratio of particles to first liquid is between 3:1 to 1:3.

While the present disclosure has been described in connection with preferred embodiments thereof, those of ordinary skill in the art will recognize that many modifications and variations are possible. For example, it is contemplated that the highly charged polymeric spheres of the present disclosure can find useful practical applications in connection with drug delivery and contrast agent diagnostics. In addition, the diffraction efficiencies enable the embedded 2-D arrays to be used for visually attractive paints and coatings, sensors, and as anti-counterfeiting film.

BRIEF DESCRIPTION OF THE SEVERAL VIEWS OF THE DRAWINGS

For the present disclosure to be easily understood and readily practiced, the present disclosure will now be described for purposes of illustration and not limitation in the connection with the following figures, wherein:

FIG. 2b shows the calculated polycrystal 2-D array PC diffraction pattern for conditions shown in FIG. 2a.

DETAILED DESCRIPTION OF PREFERRED EMBODIMENTS OF THE INVENTION

In the following detailed description, reference is made to the accompanying examples and figures that form a part hereof, and in which is shown, by way of illustration, various preferred embodiments in which the inventive subject matter may be practiced. These embodiments are described in sufficient detail to enable those skilled in the art to practice them, and it is to be understood that other embodiments may be utilized and that structural or logical changes may be made without departing from the scope of the inventive subject matter. Such preferred embodiments of the inventive subject matter may be referred to, individually, and/or collectively, herein by the term "invention" merely for convenience and without intending to voluntarily limit the scope of this application to any single invention or inventive concept if more than one is in fact disclosed.

The following description is, therefore, not to be taken in a limited sense and is intended to incorporate the entire disclosure hereof including the description of the invention, and the scope of the inventive subject matter is defined by the appended claims and their equivalents.

Figure 1A:
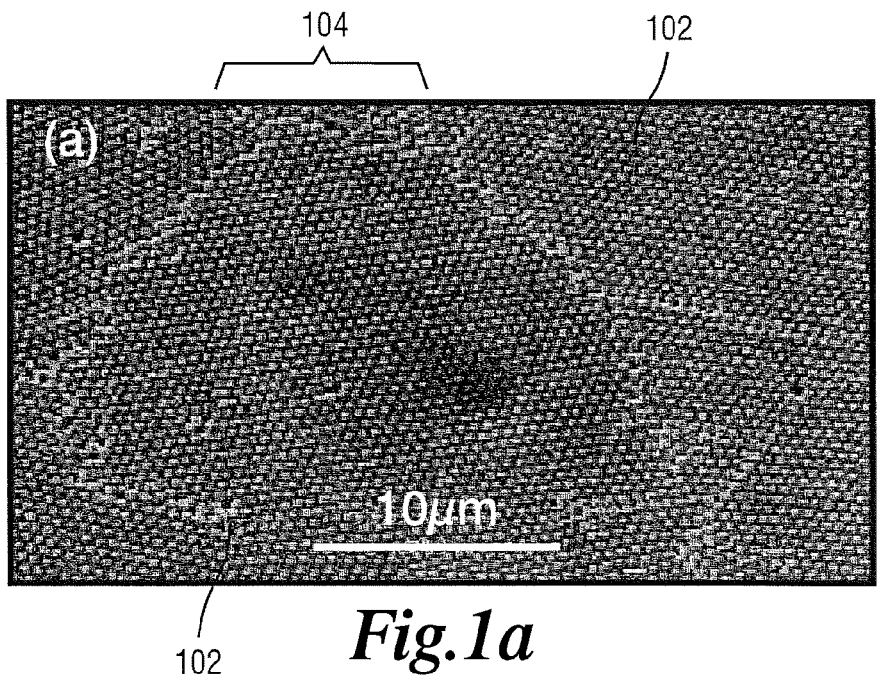
FIG. 1a and FIG. 1b depict SEM images of 2-D photonic crystals of preferred embodiment(s) of the invention.
Figure 1B:
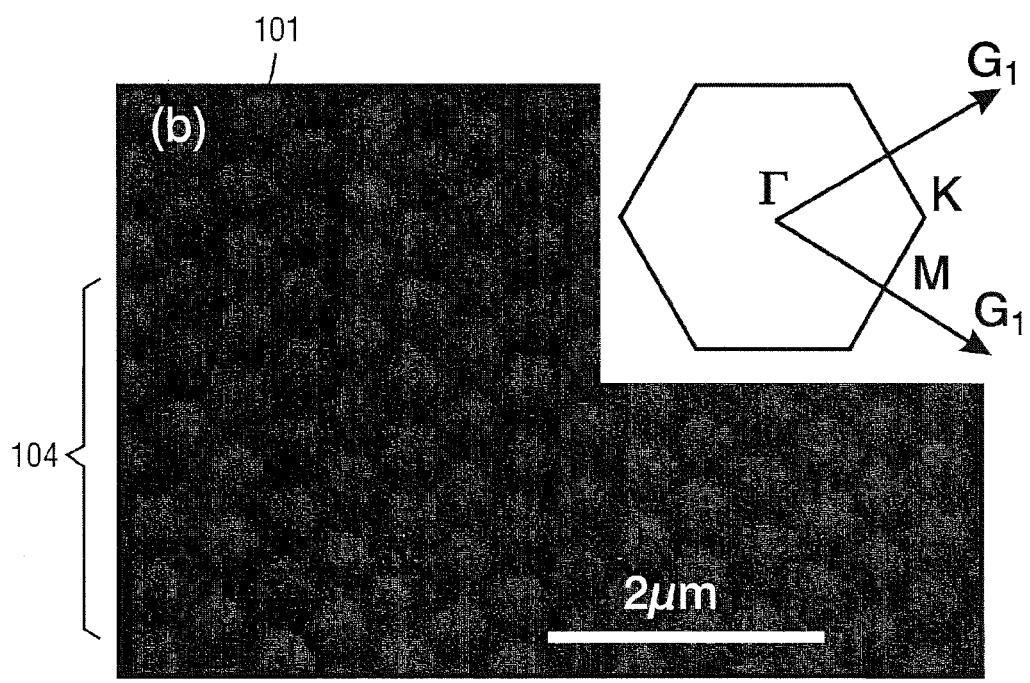

FIG. 1a and FIG. 1b are scanning electron microscope (SEM) images of 2-D photonic crystals (PC) on plastic sheet comprising 489±11 nm diameter highly charged polystyrene particles synthesized by emulsifier free emulsion polymerization. This 2-D array PC was fabricated on a liquid mercury (Hg) surface by self-assembly of these particles into a 2-D monolayer.

The 2-D array PC shown in FIG. 1a and FIG. 1b was prepared by spreading a solution containing 300 µL of a 14.37% weight fraction of colloidal particles in deionized water that was mixed with 200 µL of 1-propanol as a dispersing agent, 50 µL of hydroxyethylmethacrylate (HEMA), 20 µL of 20% vol. in 1-propanol of the photoinitiator diethoxyacetophenone (DEAP) and 1 mg of the cross-linker bis-acrylamide. 6.5 µL of the solution was gently dropped onto a clean Hg surface where it rapidly spread and formed an almost close packed polycrystalline 2-D colloidal crystal monolayer. The volume of solution added was designed to entirely coat the Hg surface with a close packed array of particles. Then a vinyl group functionalized thin plastic sheet was placed on top of the assembled array. This plastic sheet is manufactured by Bio-Rad Laboratories as a 65 mm×125 mm×100 µm gel support film. The 2-D monolayer was covalently attached to the plastic sheet by UV light polymerization of the HEMA surrounding the particle array. The 2-D array attached to the plastic sheet was then easily lifted from the Hg surface.

The FIG. 1a SEM shows that the polystyrene particle 101 array 104 protrudes from the plastic sheet indicating that the HEMA liquid layer coats and then polymerizes onto the plastic sheet surface. The polycrystalline 2-D particle array 104 shows randomly oriented 10-15 µm domains 102. A poly-HEMA thickness of ~320 nm was calculated from the SEM measured apparent diameter of the spheres. This thickness is close to that expected from the amount of HEMA in the spreading solution.

The array 104 was also attached to 25 mm×75 mm×1 mm glass microscope slides by a similar polymerization. Although the attachment of the array was not as strong as to the plastic sheet, with care it was possible to completely lift the array attached to the microscope slide from the Hg surface.

FIG. 1b depicts that the polymerized monolayer is an almost close-packed hexagonal array of 489±11 nm diameter polystyrene particles 101 with a nearest neighbor spacing of 535 nm. The inset shows the 2-D reciprocal lattice and the 2-D Brillouin zones with the F, K, M high symmetry points and the reciprocal lattice vectors G1 and G2.

The angular dependence of the diffraction efficiency of the 2-D array PC was measured by using a 532 nm laser beam with a diameter of ~1 mm that is much larger than the individual hexagonal 2-D crystal domain size.

Figure 2A:
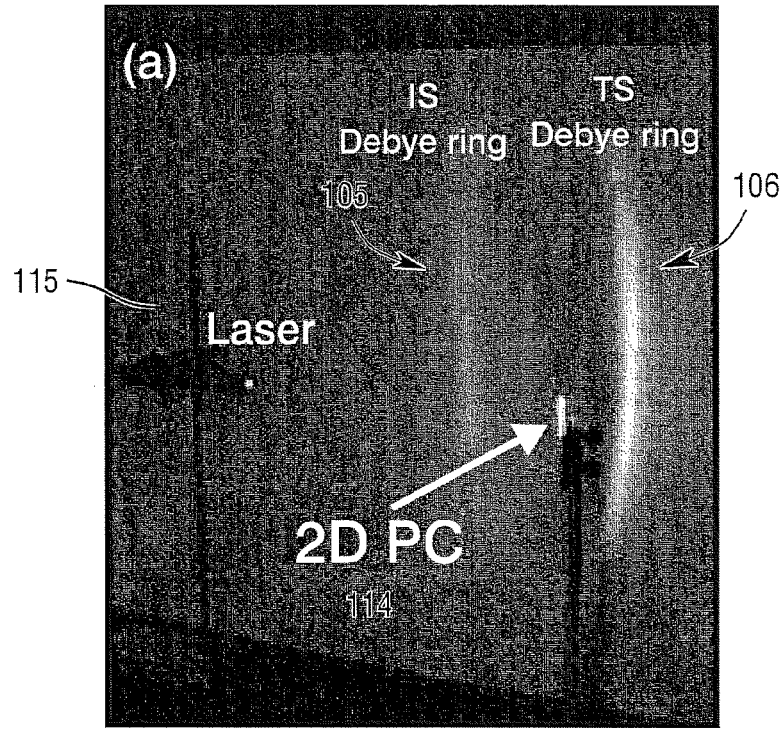
FIG. 2a shows 532 nm light diffraction from a 489 nm diameter polystyrene sphere 2-D array photonic crystals of a preferred embodiment of the invention where the light is incident at 20° from the normal and with a nearest neighboring spacing of 535 nm on a plastic sheet.

FIG. 2a shows a laser 115 projecting light beam into a 2-D PC 114 at an incident angle of ~20° from the normal and that the numerous randomly oriented domains of the two dimensional photonic crystals (2-D PC) 114 diffract light into two Debye diffraction rings 105 and 106. The intensity of the back diffracted ring 105 on the incident beam side (IS) is much less than that of the forward diffracted ring 106 on the transmitted beam side (TS).

Figure 2B:
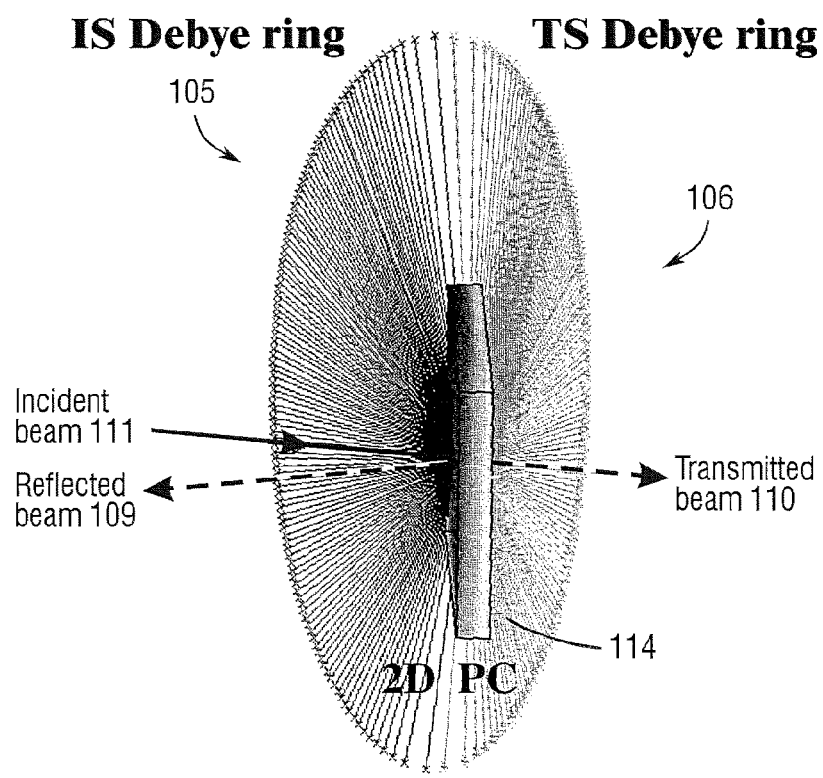

FIG. 2b is a diagram showing the calculated diffraction pattern for a 532 nm beam 111 incident at 20° from the normal to a 2-D PC 114, that has a nearest neighboring spacing of 535 nm. The orientations of the 2-D diffracted beams were calculated from 300 different equally angularly spaced orientations of 2-D array domains. The expected diffraction pattern consists of the zero diffraction order specular reflection beams 109 and transmission beams 110, and the two first order diffraction beams that form the two Debye diffraction rings. These two Debye rings are situated symmetrically about the 2-D PC 104 plane with one ring 105 on the IS of the array, while the other ring 106 occurs on the TS of the array as illustrated in FIG. 2b.

Figure 2C:
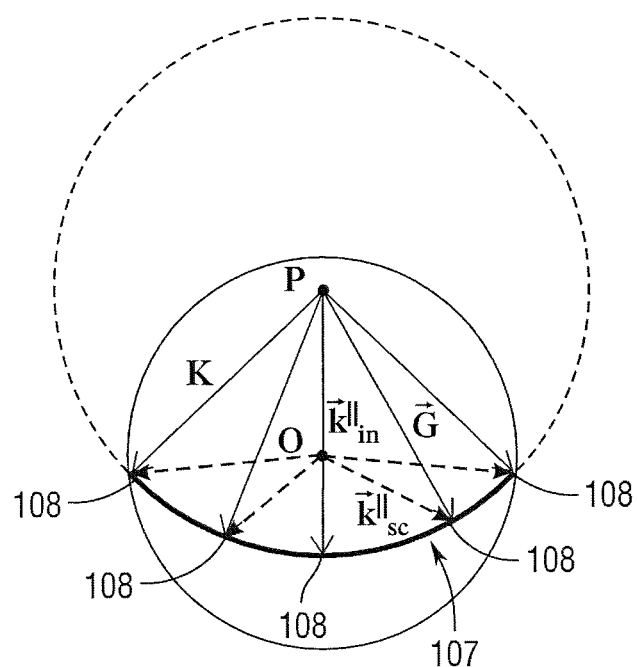
FIG. 2c shows a reciprocal space for 2-D array polycrystal diffraction of a preferred embodiment of the invention.

The 2-D diffracted beam wave vectors fulfill the kinematic theory 2-D diffraction condition:

$$\vec{k}_{sc}^{\parallel} = \vec{k}_{in}^{\parallel} + \vec{G}, \quad (1)$$

where $\vec{k}_{in}^{\parallel}$ and $\vec{k}_{sc}^{\parallel}$ are the projections of the incident and diffracted light reciprocal wave vectors into the 2-D crystal plane and $\vec{G}$ is any 2-D array reciprocal lattice vector. FIG. 2c shows the 2-D reciprocal space plane that lies in the 2-D array PC plane that contains the 2-D array reciprocal lattice vectors $\vec{G}$ and vectors $\vec{k}_{in}^{\parallel}$ and $\vec{k}_{sc}^{\parallel}$.

Figure 2D:
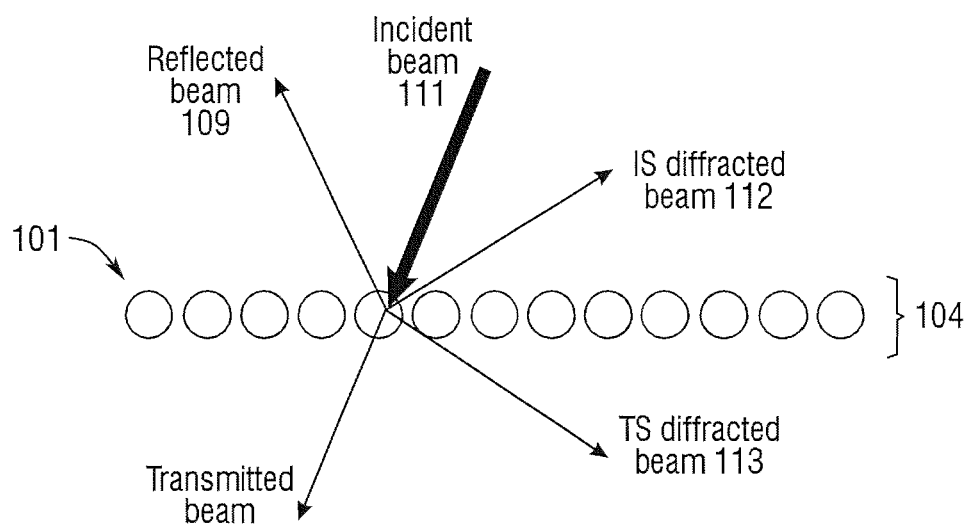
FIG. 2d is a diagram illustrating diffracted beams from one or more preferred embodiments of the invention.

In FIG. 2c the reciprocal lattice vectors $\vec{G}$ for all possible randomly oriented 2-D array crystal domains originate from the center of the circle P, and end on its circumference. The projection of the incident light wave vector into the 2-D array plane gives the incident in-plane wave vector $\vec{k}_{in}^{\parallel} = \overrightarrow{OP}$. Its length depends upon its angle of incidence. In order to satisfy equation (1) the scattered vectors $\vec{k}_{sc}^{\parallel}$ must originate at point O and end on the circle circumference. Since the projection $\vec{k}_{sc}^{\parallel}$ cannot be larger than $k=|\vec{k}_{sc}|=|\vec{k}_{in}|$, the allowed $\vec{k}_{sc}^{\parallel}$ must lie within the Ewald black circle with origin O and radius k. Therefore a Debye diffraction ring will be formed by all diffracted beams with $\vec{k}_{sc}^{\parallel}$ starting at O and ending on the bold arc 107 as defined by the dashed arrows 108. The resulting Debye ring diffraction pattern is formed by these scattered $\vec{k}_{sc}$. The light from the Debye rings illuminate two arcs along the observation plane as observed in FIG. 2a. FIG. 2d illustrates the diffracted beams 105 and 106. The incident beam 111 is transmitted towards the two dimensional photonic crystals (2-D PC) 104. A part of the beam is reflected 109 and there is the incident side diffracted beam 112 that results in the IS Debye ring 105. A portion of the beam is transmitted across the 2-D PC 104 as the transmitted beam 110. A certain portion of the transmitted beam is diffracted through the 2-D PC 104 as the Transmitted Side diffracted beam 113, that results in a TS Debye ring 106.

Figure 3A:
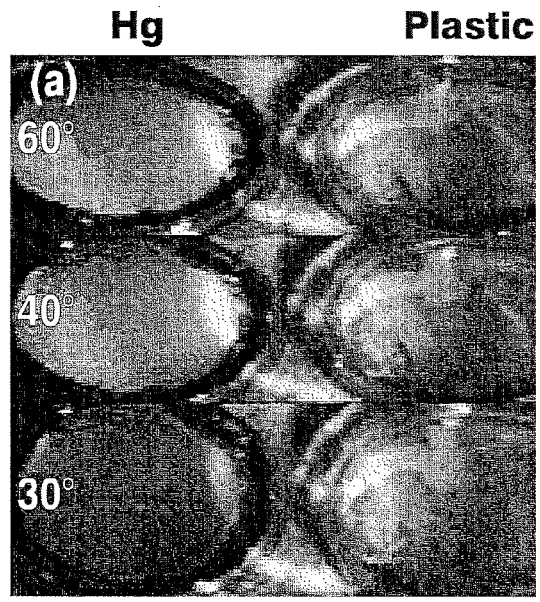
FIG. 3a shows diffraction colors for a 2-D array PC on a mercury surface according to a preferred embodiment of the invention.

FIG. 3a shows the diffracted colors from a white light beam incident at 30° from the normal onto a 2-D array spread on a Hg surface (left) and on a plastic sheet (right) at different viewing angles. The diffracted light wavelength decreases as the viewing angle moves towards the array normal, as expected for 2-D diffraction. The brightness of the 2-D diffraction pattern for the 2-D array PC on the Hg is obviously much higher than from the array on a plastic sheet.

Figure 3B:
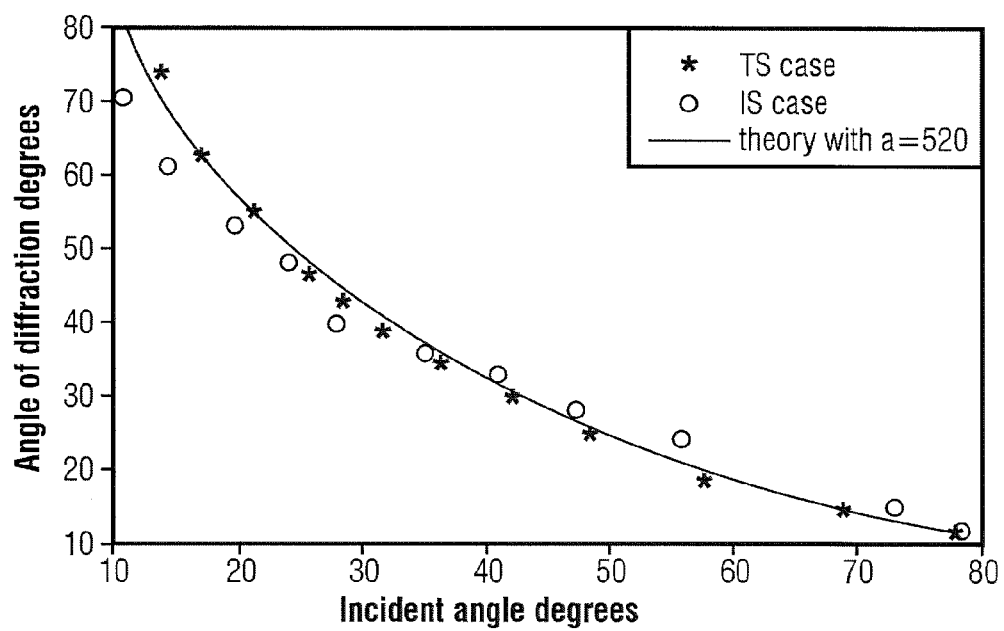
FIG. 3b is a chart showing incident angle against angle of diffraction for a 2-D array PC on a plastic sheet according to a preferred embodiment of the invention.

FIG. 3b shows the measured and calculated dependence of the diffraction angle in the plane of the 2-D array PC normal and the ΓM symmetry axis (FIG. 1b) of the 2-D Brillouin zone of a hexagonal lattice on the incident angle. This measurement is for diffraction from the 2-D array attached to a plastic sheet. The diffraction occurs from domains oriented with their ΓM direction within this plane. Both $\vec{k}_{in}^{\parallel}$ and $\vec{k}_{sc}^{\parallel}$ are parallel to the reciprocal lattice vector $\vec{G}$. The 2-D diffraction condition is $|\vec{k}_{sc}^{\parallel}| + |\vec{k}_{in}^{\parallel}| = |\vec{G}|$ which gives $$m\lambda = d\frac{\sqrt{3}}{2}(\sin(\alpha_{dif}) + \sin(\alpha_{in})),$$

where d is the spacing between nearest neighboring particles, m is the diffraction order and $\alpha_{in}$ are $\alpha_{dif}$ are the incident and diffracted angles from the normal. The measured diffracted angles for both the TS and IS (relative to the 2-D PC plane) diffracted light agree well with those calculated for d=520 nm (FIG. 3b).

Figure 3C:
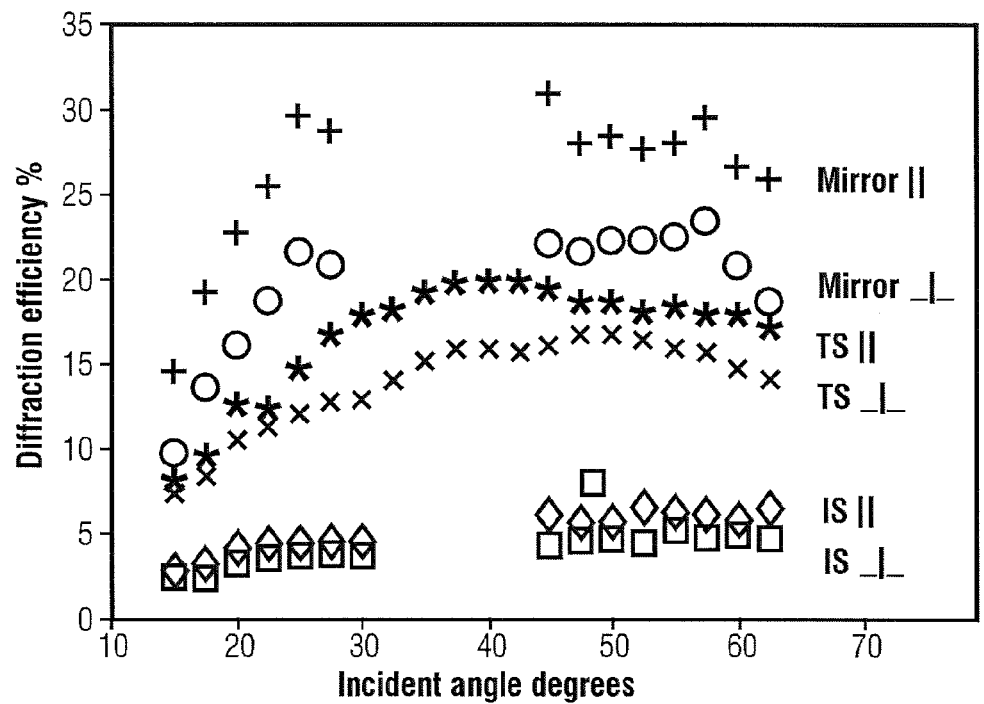
FIG. 3c shows incident beam angular dependence of IS and TS diffraction.

FIG. 3c shows the measured angular dependence of the diffraction efficiency of a 532 nm laser beam from the 2-D array PC attached to a glass microscope slide in the case that the diffracted beam lies in the same plane as the incident beam and the 2-D plane normal. The intensity diffracted into the Debye ring was estimated by measuring the intensity diffracted into a small area of the Debye ring and then dividing this intensity by the relative fraction compared to the total ring. The intensity per unit area measured from different regions of the Debye ring is relatively constant, varying by <20%.

Figure 3D:
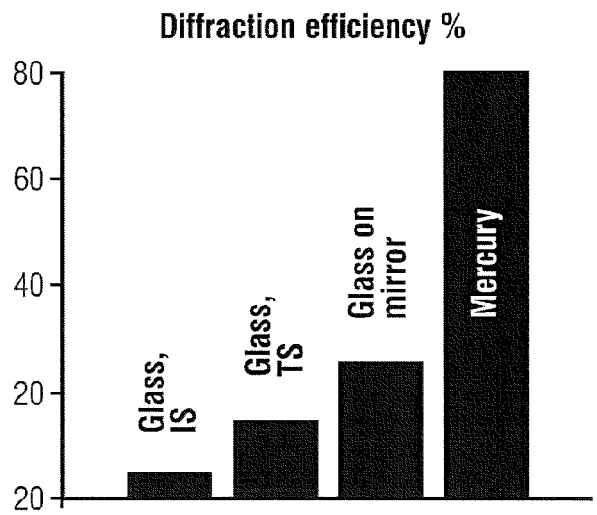
FIG. 3d shows 25 deg incident angle parallel polarization IS and TS diffraction efficiencies from 2-D array PC on glass slide according to a preferred embodiment of the invention.

FIG. 3d represents the results for a 532 nm parallel polarized beam incident at 25° from the normal to the 2-D array PC on the glass slide, a diffraction efficiency of 4.5% was measured for the IS and 15% for the TS Debye rings. In contrast, a 30% diffraction efficiency was measured (which is larger than the sum of the TS and IS diffracted intensities in the absence of the mirror) from the same 2-D array PC on the glass slide when its glass (no 2-D array) side was placed on a front surface aluminum mirror. A 2-D array PC self assembled on the Hg showing an even larger diffraction efficiency of ~80% at the same angle. This increased IS diffracted efficiency from the 2-D array PC spaced from the Al mirror by 1 mm glass thickness can be easily rationalized by using the single particle scattering approximation for dielectric spheres on a dielectric substrate, or for dielectric spheres spaced at least ~5 wavelengths away from a metal surface.

Figure 4:
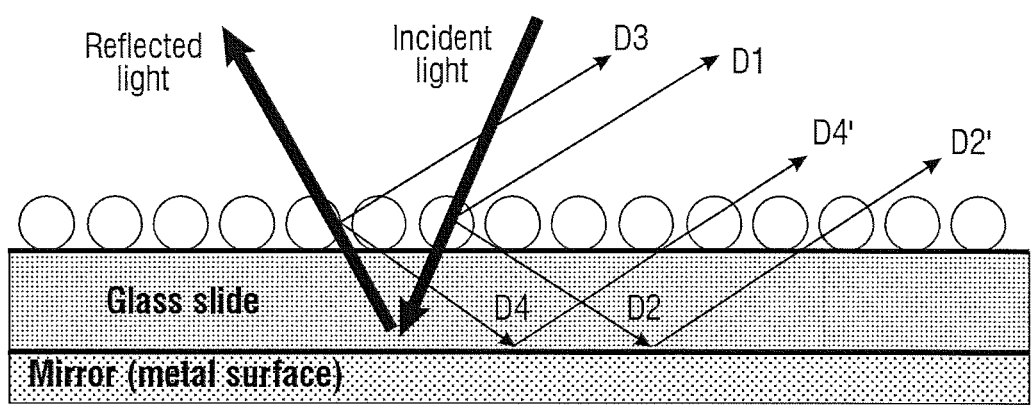
FIG. 4 depicts a diffraction from a 2-D array photonic crystals separated by a layer of glass from a mirror according to a preferred embodiment of the invention.

In this model the scattering of the 2-D sphere array spaced by the glass slide from the metal mirror results from a combination of diffraction and reflection processes. FIG. 4 depicts that light incident on the 2-D array PC diffracts into IS and TS beams D1 and D2. The TS diffracted beam D2 is then reflected by the mirror to form beam D2' which is parallel to D1. The incident light transmitted through the 2-D array PC is reflected by the mirror and diffracts from the 2-D array PC, resulting in the diffracted beam D3 that also propagates parallel to D1. The diffracted beam D4 is reflected forming D4' that also propagates parallel to D1. The total diffracted intensity is D1+D2'+D3+D4'. In contrast, for the 2-D PC on glass slide only diffracted beam D1 is observed. The increased diffraction intensity observed with the mirror results from the additional contribution of the TS diffraction and because in accordance with preferred embodiments of the invention TS diffraction is much larger than IS diffraction.

FIG. 3c shows that for incident angles between 15° to 65° for the 2-D array PC on the glass slide the TS diffracted light intensity is 2 to 2.5 times larger than the IS diffracted light. The dominance of TS diffraction over the IS diffraction results from the Mie scattering of these spherical particles as shown by FIG. 5a that shows the Mie single sphere scattering diagram for a dielectric sphere of 490 nm diameter with a refractive index of 1.58 in an air-HEMA medium with an estimated volume averaged refractive index of 1.26.

Figure 5A:
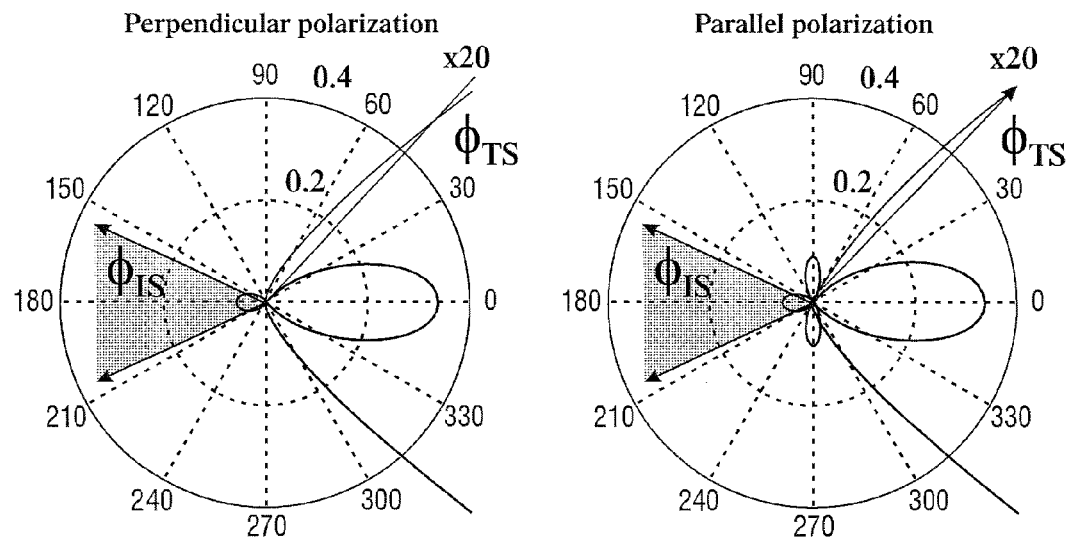
FIG. 5a shows 532 nm light scattering Mie diagrams for a 490 nm diameter sphere of refractive index.

FIG. 5a is a Mie scattering diagram showing the dependence of scattered intensity on the scattering angle, where differential scattering cross section per unit solid angle is plotted. The Mie scattering is strongly asymmetric with forward scattering much stronger than backward scattering. The perpendicular polarized backward scattered intensity efficiently occurs as a single small lobe with a maximum in the exact backward direction of 180°. The parallel polarized backward scattered intensity shows that strong dependence on the scattering angle occurs as three lobes.

To determine the scattering efficiency at diffraction direction for the spheres within the 2-D array, the effective single scattering angles $\phi_{IS}(\phi_{TS})$ between incident and IS (TS) diffracted directions must be determined. These scattering angles are $\phi_{IS}=\alpha_{dif}-\alpha_{in}$ and $\phi_{TS}=180°-\alpha_{dif}-\alpha_{in}$, where the incident and diffraction angles $\alpha_{in}$ and $\alpha_{dif}$ that are defined relative to the 2-D PC normal are calculated by including Snell's law refraction between the air into the dielectric medium, consisting of the polystyrene particles in the thin HEMA layer. Snell's law refraction accounts for the fact that the local field incident on the individual spheres is a combination of the incident field and the scattered fields from all other monolayer spheres. The contribution is approximate of the other spheres by invoking an effective medium approximation and calculating the directions of the local incident and local scattered fields as if individual spheres are embedded into a homogeneous layer with an effective volume averaged refractive index. FIG. 5a depicts 532 nm light scattering Mie diagrams for a 490 nm diameter sphere with refractive index of 1.58 in a medium of refractive index 1.26 shows differential scattering cross section (with units $\mu m^2$) per solid angle. Left is for perpendicular polarized light, right is for parallel polarized light. Range of TS and IS single sphere scattering angles corresponding to a 15° to 65° range of incident angles is indicated by the triangular section $\Phi_{IS}$.

Figure 5B:
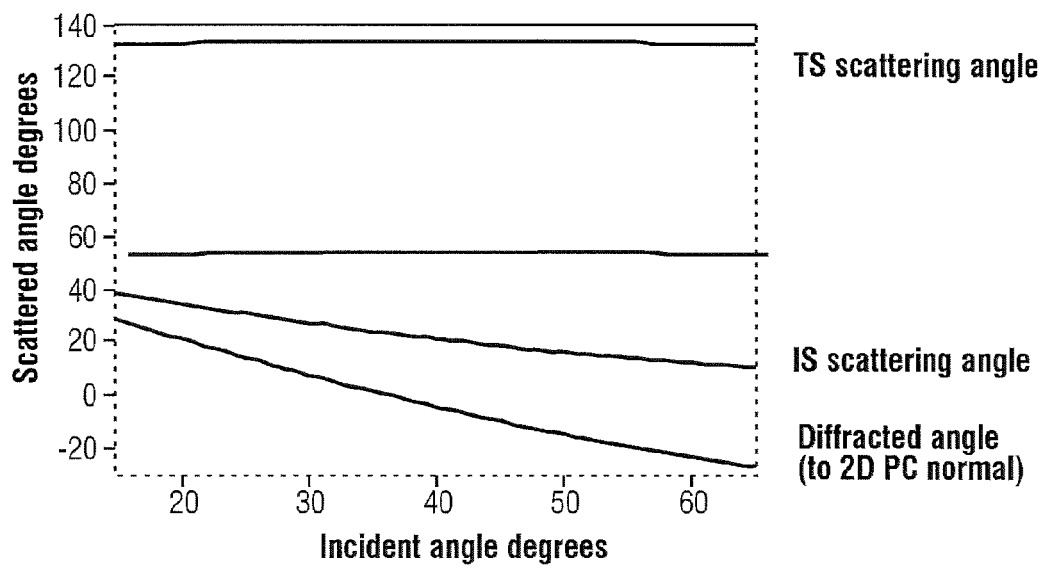
FIG. 5b shows a chart comparing scattered angle against incident angle.

FIG. 5b shows the dependence of the IS and TS calculated scattering angles $\phi_{IS}$ and $\phi_{TS}$ on the incident angle. For incident angles between 15° to 65° the TS scattering angle $\phi_{TS}$ remains approximately constant at ~133°, and the corresponding single sphere differential cross section is ~0.025 (~0.03)$\mu m^2$ for perpendicular (parallel) polarizations (the bottom curve in FIG. 5a, designated as Diffracted angle to 2-D PC normal). For the same range of incident angles 15°-65° the IS scattering angle $\phi_{IS}$ varies between −25° and 25°, and the corresponding differential cross section is between ~0.002 to ~0.003 $\mu m^2$ for both perpendicular and parallel polarizations. The large increased single sphere scattering power in the TS direction relative to the IS direction explains the observed data of FIG. 3b.

This section shows that for the first time the diffraction efficiency of light was measured from a dielectric 2-D array PC on dielectric and metal substrates. Almost close packed 2-D polystyrene particle arrays were prepared by solvent evaporation of self assembling monolayer on a Hg surface. The 532 nm light diffraction efficiency from 2-D array PC on glass slide in the TS direction was measured to be 3 to 4 fold larger then in the IS direction. This difference is due to large differences in Mie scattering intensities of single sphere scattering. Diffraction efficiency reaches 30% for 2-D array PC on glass slide on top of mirror and 80% for 2-D array PC on Hg.

Figure 6:
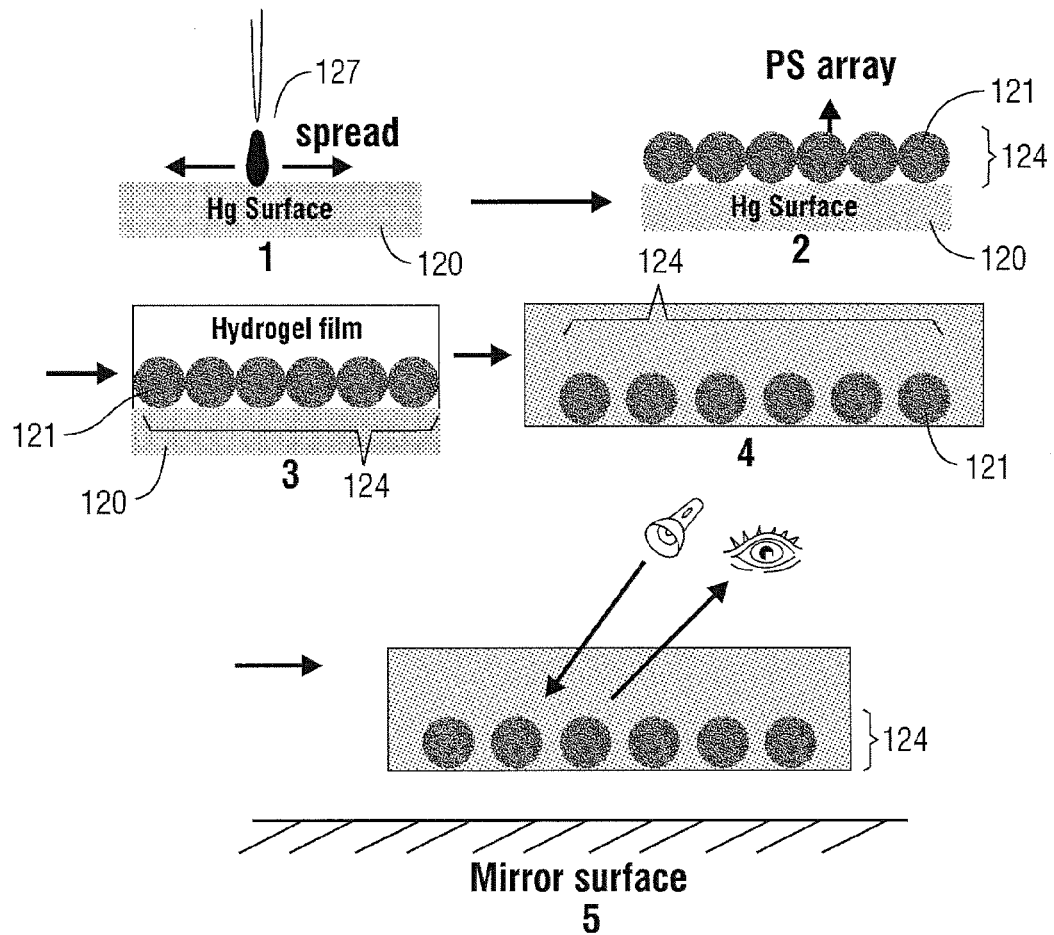
FIG. 6 comprises sequential views showing a fabrication of a 2-D photonic crystal for sensing application according to a preferred embodiment of the invention.

An alternative preferred embodiment of the present invention in FIG. 6 shows the fabrication of the 2-D colloidal crystal array (CCA) attached to a hydrogel. First a well-ordered 2-D close-packed array of 580 nm diameter polystyrene (PS) spheres 121 are prepared on a mercury (Hg) surface 120. This is accomplished by placing a drop of a PS particle aqueous/propanol dispersion (13.3% w:v) onto a Hg surface. Because moderate surface tension liquids spread readily on Hg 120 as thin films, the colloid particle suspension spreads rapidly during which the 2-D PS particle monolayer self-assembles as the solvent evaporates. In FIG. 6 at 1 the water/propanol PS particle dispersion 127 is dropped onto Hg surface 120. In FIG. 6 at 2 the dispersion spreads to form a 2-D close-packed PS particle 121 array 124 as solvent evaporates. FIG. 6 at 3 depicts the polymerization of hydrogel film around 2-D array 124. At 4, the swelled hydrogel with embedded 2-D array was peeled off from the glass substrate and in FIG. 6 at 5 diffraction from the 2-D array-hydrogel sandwich is depicted. Various preferred embodiments of the invention foresee the 2-D array may be fully embedded in the polymer or may be substantially embedded, wherein the particles of the 2-D array are not fully embedded in the polymer.

Figure 7A:
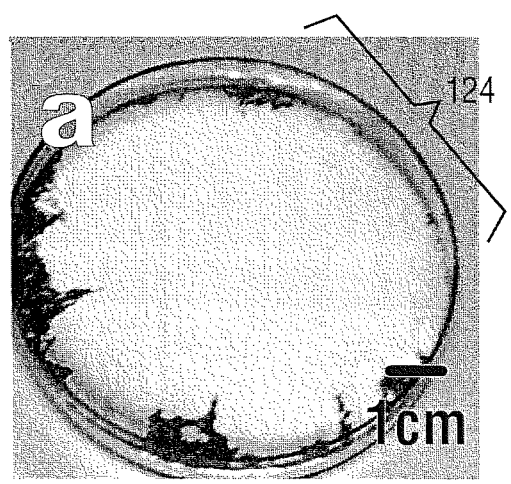
FIG. 7a shows bright diffraction of yellow light from a PS particle array on Hg surface.
Figure 7B:
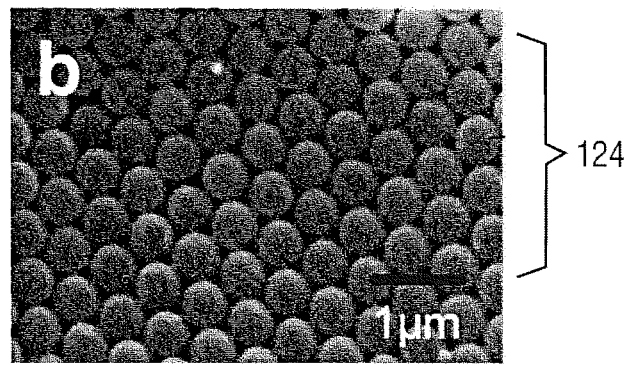
FIG. 7b is SEM image of 2-D PS array transferred onto a plastic sheet after sputter coating with Au according to a preferred embodiment of the invention.

FIG. 7a shows that the self assembled ordered 2-D monolayer brightly diffracts over 8% of the incident light back towards the observer. The array 124 was illuminated by white light at an incident angle of 27° and observed at 45° from the normal. FIG. 7b shows an SEM image that demonstrates high order of the hexagonal 2-D array 124 of PS spheres 121 that self-assembled on the Hg surface with a domain size of ~10 $\mu m$. The PS array is transferred onto a plastic sheet after sputter coating with gold (Au). This is the first observation of high efficiency 2-D diffraction from 2-D arrays on Hg surfaces. Preferably, the metal surface may also be gold, silver, aluminum, copper, iron, steel, or reflective alloy.

Figure 7C:
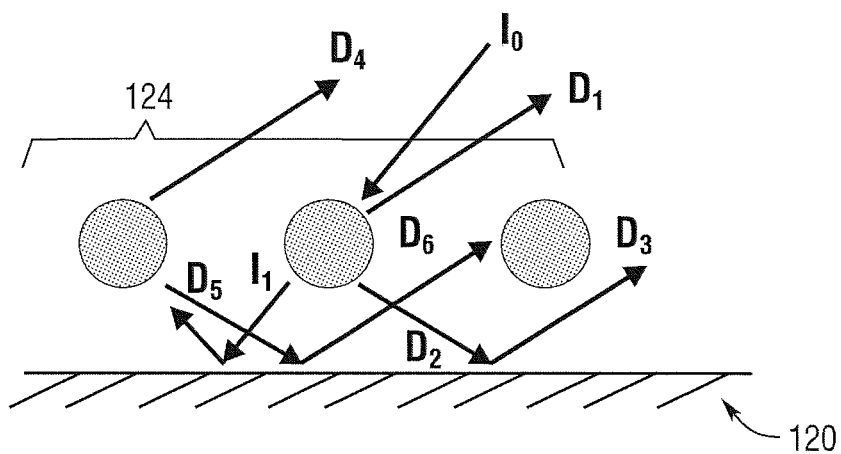
FIG. 7c depicts a preferred mechanism of the invention giving rise to strong diffraction.

FIG. 7c represents the very bright diffraction results from the combined diffraction of four beams. The 2-D array 124 diffracts the incident light ($I_0$) back towards the observer on the incident side giving rise to a rather weak diffracted beam $D_1$. The more intense 2-D array forward diffracted beam, $D_2$, is back reflected to the observer by the Hg surface, forming the intense $D_3$ beam that propagates parallel to $D_1$. In addition, the remaining incident light is transmitted (IL zero order diffracted) through the 2-D array and is back reflected by the mirror. This beam is forward diffracted by the 2-D array forming the diffracted incident beam $D_4$ that also propagates parallel to $D_1$. The back diffracted beam $D_5$ is reflected to from beam $D_6$ which also propagates parallel to $D_1$. The total diffracted light results from summation of intensities of beams $D_1$, $D_3$, $D_4$ and $D_6$; the total intensity is comparable to that of the incident light. The detailed mechanism quantitatively explaining the high diffraction efficiency is presented herein.

Figure 8:
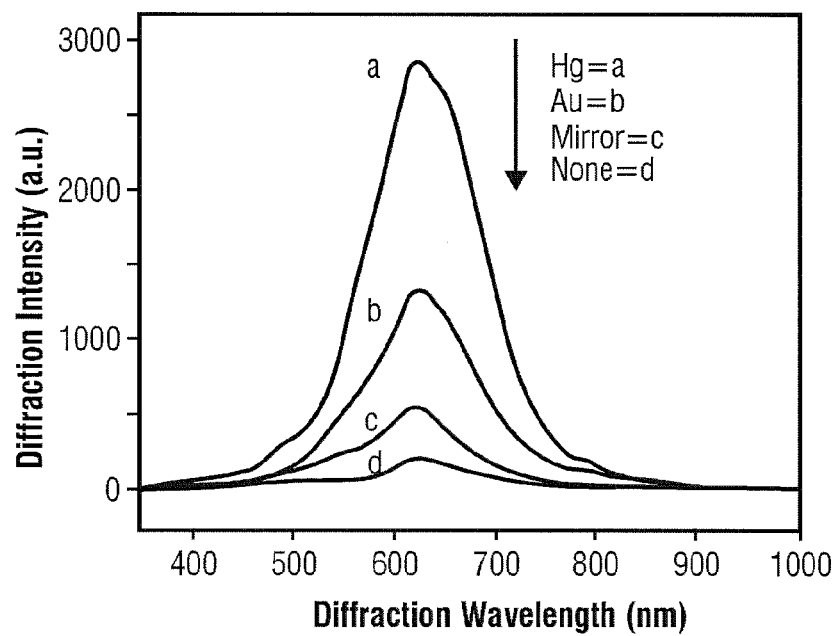
FIG. 8 depicts diffraction of 2-D arrays on different mirror surfaces according to various preferred embodiment of the invention.

The diffraction is probed by using a six around one reflection probe where one central fiber is excided excited with white light and the back diffracted light is collected with a closely surrounding set of six fibers in a Littrow configuration. FIG. 8 compares the diffracted intensity of a PS 2-D array on a transparent plastic film to the diffracted intensity of this film placed on Hg and other mirror surfaces. In FIG. 8, line a is Hg, line b is Au, line c is commercial glass surface mirror and line d is plastic film. Here, the measurement angle between the probe and the normal to the 2-D array was 38°. The diffracted intensity from the 2-D array on the Hg surface was 15-fold larger than that form the 2-D array on the plastic film indicating the strong reflection enhancement. Other flat reflective surfaces also increase the diffracted intensity. For example, FIG. 8 shows that a flat gold reflector b and a glass surface mirror c increase the diffraction efficiency 6-fold and 2.7-fold compared to the plastic film d. The metal surface may preferably be gold, silver, aluminum, copper, iron, steel, or reflective alloy. The resulting very bright back reflection makes it easy to visually or instrumentally monitor the 2-D array diffraction.

For most sensing applications it would be preferable to utilize a non-close-packed array, so that the particle spacing can both swell and shrink while attached to a hydrogel that is responsive to specific analyte concentrations. A non-close-packed sensing array was fabricated by transferring the 2-D array onto a hydrogel that contains molecular recognition agents (See FIG. 6). The molecular recognition agents are designed to cause reversible hydrogel swelling/shrinking due to analyte introduced alterations in the hydrogel osmotic pressure that forces changes in the 2-D lattice spacing that causes shifts in the diffracted wavelength.

The 2-D array was transferred onto a thin hydrogel layer attached to a glass slide by polymerization of 1 ml aqueous solution containing 10 wt % acrylamide (AAm), 0.2 wt % N,N-methylenebis(acrylamide) (MBAAm), 20 µL acrylic acid (AAc) and 10 µL Irgacure 2959 [in DMSO, 33% (w:v)]. A glass slide (60 mm×24 mm×0.12 mm) was placed on the polymerization solution on top of the 2-D array. The glass slide displaced excess polymerization solution from the top of the 2-D array.

The polymerization was initiated by UV light from a Blak-Ray lamp (265 nm, 5 to 10 min) The resulting hydrogel film-embedded 2-D array was removed from the Hg surface by lifting the glass slide. This hydrogel film-embedded 2-D array was peeled off the glass slide and rinsed with large amounts of $H_2O$. Alternatively, the crown ether containing hydrogel film-embedded 2-D array was fabricated by replacing the AAc with 30 µl of 4-acryloylamidobenzo-18-crown-6 (4AB18C6) in DMSO solution (w:v=1:2).

Figure 9A:
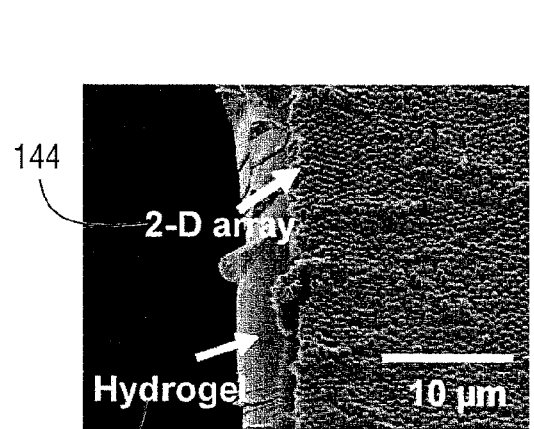
FIG. 9a is a SEM image of PS array on PAAm-AAc hydrogel film.
Figure 9B:
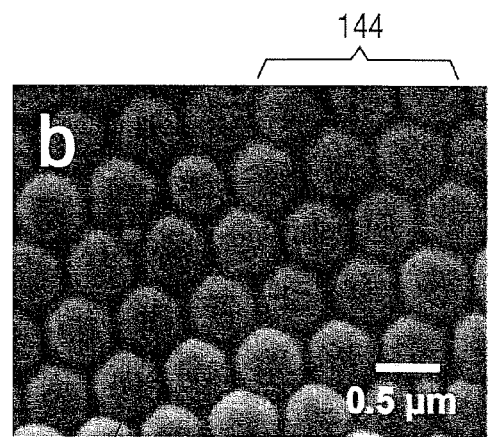
FIG. 9b is a high resolution SEM image of 2-D PS array on PAAm-AAc hydrogel.

FIG. 9a shows an SEM image of the air-dried 2-D array 144 on the poly(acrylamide-co-acrylic acid) (PAAm-AAc) hydrogel 145 on the glass slide. FIG. 9b shows that the polymerized hydrogel was localized at the glass interface with the PS particle 141 array 144 protruding from the hydrogel. Analysis of the SEM image in FIG. 9d indicated that the 2-D ordering was not significantly degraded by the polymerization and transfer process.

Figure 9C:
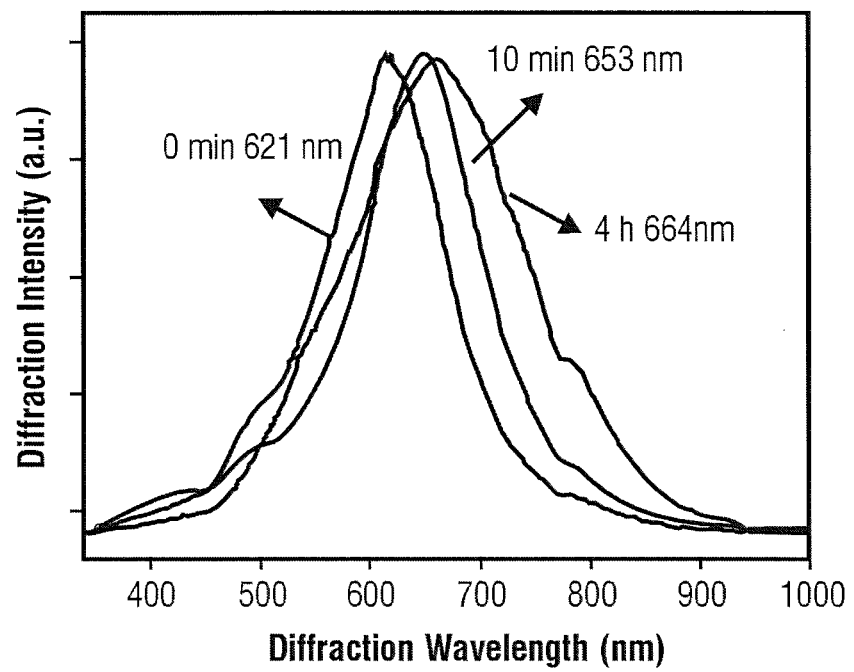
FIG. 9c is a table depicting back diffraction of close packed 2-D arrays against non-close packed 2-D arrays.
Figure 9D:
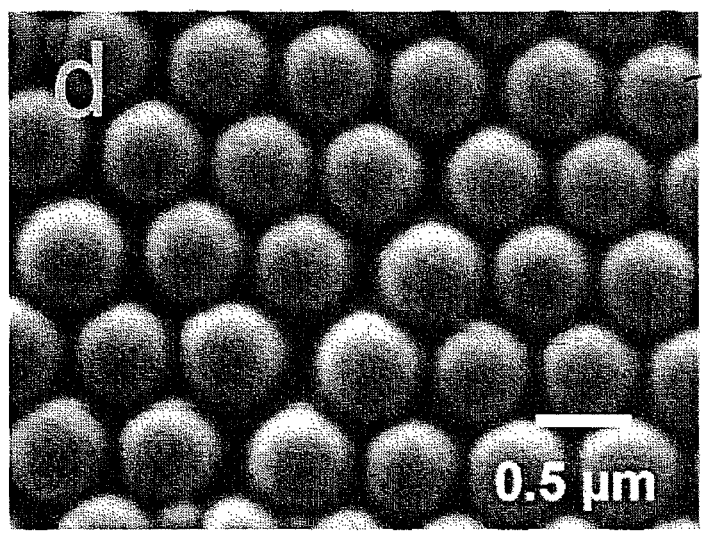
FIG. 9d is a high resolution SEM image of the non-close packed PS particles in swollen PAAm-AAc hydrogel.

FIG. 9c is a chart depicting the results of placing this 2-D-array-containing hydrophilic hydrogel in water which swelled the hydrogel and increased the 2-D array spacing, which produced a red shift in the diffraction; within 10 min, the diffraction was red-shifted from 621 to 653 nm, and it reached equilibrium at 664 nm in less than 30 min FIG. 9d shows an SEM image of the PS particle 141 array 144 on the PAAm-AAc hydrogel (not shown) that had previously been swollen in water. The swollen 2-D-array-containing hydrogel film was allowed to dry while physically restrained to prevent the central area from shrinking on drying. This maintained the hydrated 2-D particle array spacing.

In a preferred embodiment of the invention, the polymer is a hydrogel polymer. In preferred embodiments, the 2-D array hydrogel is affixed by a second polymerization with components on a face of the solid reflective surface. In other preferred embodiments, the second polymerization has less cross-linking than in the polymer. In additional preferred embodiments the second polymerization has longer polymer lengths than found in the polymer. In additional preferred still more embodiments, the spacing of the 2-D array may be expanded such that the embedded or substantially embedded 2-D array of particles is no longer close packed. The surface area of the polymer may be expanded such that the embedded or substantially embedded 2-D array of particles is no longer close packed, and then restrained from reforming a close packing of particles, e.g. by physical means such as drying, stretching of the polymer, or by physical or chemical means by the affixing to an article of manufacture.

In the Littrow configuration, the 2-D Bragg diffraction relationship is $m\lambda = 3^{1/2} d \sin \theta$, where m is the diffraction order, $\lambda$ is the diffracted wavelength (in vacuum), d is the 2-D particle spacing, and $\theta$ is the angle of the light relative to the normal to the 2-D array. The 2-D diffracted wavelength is independent of the refractive index. The diffraction studied here resulted from the shortest 2-D reciprocal lattice vector. Thus, for a defined $\theta$, $\lambda$ was proportional to the spacing between particles. Based on the experimental data, it was calculated that $\lambda_{dried}/d_{dried}=(621 \text{ nm})/(580 \text{ nm})=1.072$, which is quite close to the value $\lambda_{swollen}/d_{swollen}=(662 \text{ nm})/(622 \text{ nm})=1.064$, demonstrating that the diffraction wavelength varied with the particle spacing.

Figure 10A:
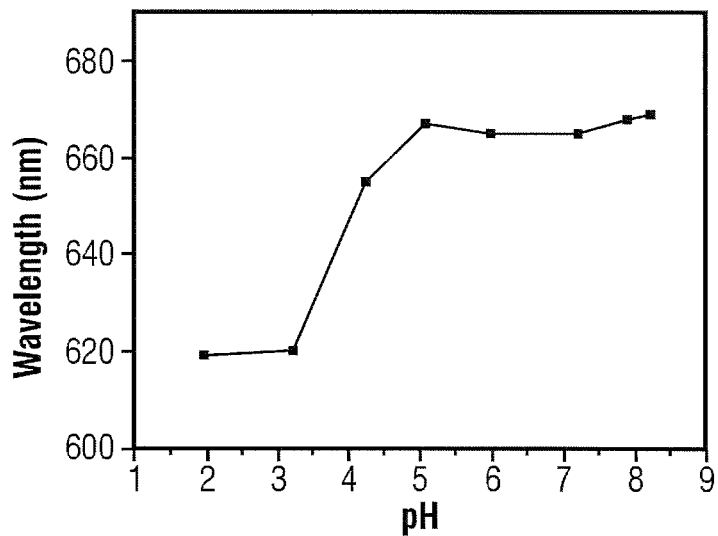
FIG. 10a is a graph of pH dependence of diffraction wavelength of 2-D arrays.

AAc was copolymerized into the hydrogel to fabricate a pH responsive material. FIG. 10a shows the pH dependence of the diffraction from this 2-D array in a buffer solution containing 150 mM NaCl. As shown in FIG. 10a, the diffraction was red-shifted from 620 nm to 668 nm between pH 3.22 and 7.91 as the AAc carboxyl groups became ionized. The change in color was clearly and visually evident. Carboxyl group ionization immobilized counterions within the hydrogel, resulting in an osmotic pressure due to the increased Donnan potential that swelled the hydrogel, as observed earlier for 3-D photonic crystals. These pH diffraction shifts were fully reversible over multiple pH cycles.

Figure 10B:
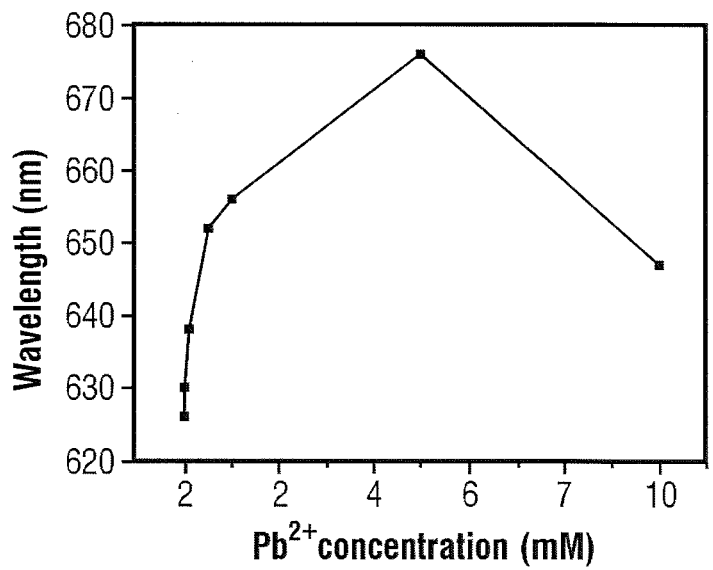
FIG. 10b is a graph of $Pb^{2+}$ dependence of diffraction wavelength of 2-D arrays in PAAm-4AB18C6 hydrogel after equilibrium at different concentrations of $PB^{2+}$ in water.
Figure 10C:
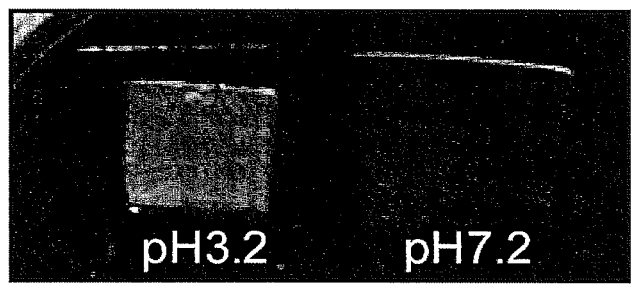
FIG. 10c is a view at an angle of 38° to the 2-D array normal showing differences of the 2-D PS array hydrogels at pH 3.2 and pH 7.2.

FIG. 10b shows the dependence of the diffraction wavelength on the $Pb^{2+}$ concentration. A 2-D sensing material for monitoring of $Pb^{2+}$ was also fabricated by copolymerizing 4AB18C6 into the hydrogel. This crown ether selectively complexes $Pb^{2+}$ to immobilize charge onto the hydrogel, which also results in an increased osmotic pressure due to the Donnan potential arising from the mobile counterions, just as in the pH sensor. The $Pb^{2+}$ binding forms a polyelectrolyte hydrogel whose charge state is determined only by the number of bound $Pb^{2+}$ ions. The swelling of the hydrogel increases with the number of attached charged groups. The measurement angle between the probe and the normal to the 2-D array was 38°. Below 5 mm, the diffraction was red-shifted with increasing $Pb^{2+}$ concentration, while above 10 mm, the diffraction was blue-shifted. This occurred because the crown ethers were saturated above 5 mm $Pb^{2+}$ and further increases in $Pb^{2+}$ concentration resulted in a decreased Donnan osmotic pressure at higher ionic strengths. FIG. 10c clearly shows the visually evident color changes that occur with changing pH values.

Preferred embodiments of the invention are possible with compounds such as, but not limited to, urea, uric acid, antigens, and antibodies; cations such as, but not limited to, sodium, potassium, calcium, magnesium, mercury, and ammonia; and for anions such as, but not limited to, chloride, carbonate, bicarbonate, and phosphate are used in place of carboxyl groups as chemical sensors. Additionally, chemical sensors for cations and anions may incorporate chelating agents into the polymer, where the chelating agents may include crown ethers, azacrown ethers, borane complexes, calixarene, and cation selective binding proteins.

These 2-D photonic crystal sensors are capable of detecting extremely small quantities of analytes. For example, utilizing a visually evident sensor with an area of 1 $mm^2$ attached to a 10 μm thick hydrogel layer, enabled the sensing of a sample volume of ~$10^{-5}$ ml. FIG. 10b indicates a detection limit of much less than 0.1 mm $Pb^{2+}$. Thus, <$10^{-12}$ mol of $Pb^{2+}$ can be detected.

These 2-D arrays have multiple advantages over previous 3-D photonic crystals. For example, the 2-D array hydrogel can be functionalized with molecular recognition agents prior to attachment of the 2-D array. In the case of the 3-D CCA, the functionalization chemistry must be homogeneous to avoid disordering the 3-D array. In addition, only the 2-D array spacing is monitored on micrometer-thick films. Such thin films allow fast detection of small volumes because of rapid diffusion. It is not necessary to utilize self-assembled colloidal particle arrays; any 2-D array of sufficient refractive index modulation will work.

Preferred embodiments of the invention may incorporate an ultrahigh-diffraction efficiency 2-D particle array materials that can be utilized for chemical sensing. These hydrogel films can be tailored to detect many molecular analytes and biological agents and preferably these 2-D photonic sensing materials will find applications in visual chemical detection systems and methods.

In preferred embodiments, the invention may incorporate the preparation of close packed 2-D arrays. A preferred fabrication method uses Hg as the substrate for particle self assembly. 2-D PS arrays were preferably fabricated by spreading PS particle suspended in water/organic mixed solvent. Organic solvents with low surface tension were preferably introduced into the PS aqueous suspension before dropping onto Hg surface. The addition of these organic solvents preferably does not disrupt the colloid ordering or cause aggregation in the liquid phase.

The concentration of PS particles and the ratio between PS aqueous colloid suspension and organic solvents preferably may be varied in a broad range. The present disclosure shows an investigation of PS aqueous/PrOH suspensions have been investigated with different volume ratios from 3:1, 2:1, 1:1, 1:2, to 1:3. With these ratios, well ordered and bright 2-D colloidal arrays on Hg have been obtained.

A preferred procedure for the growing of 2-D particle array can be applied to different suspension of particles with different size and materials. 2-D arrays of PS particles that have a diameter varying from 100 nm to 2 μm were fabricated. These sizes are in the major diameter ranges of systems with considerable scientific and practical importance. In addition inorganic particles, such as silica spheres, were spread on the surface of Hg to form 2-D colloidal arrays.

Another approach to form ordered, close packed 2-D particle arrays on water surface according to a preferred embodiment of the invention uses the Marangoni effect in water, where a surface layer can be induced to rapidly spread across a water surface if species in the applied surface layer decrease the water surface tension. The addition of propanol, for example, to the PS suspension particles in water causes rapid spreading of the 2-D array. The area size of the 2-D arrays can be tailored up to 100 $cm^2$ by just controlling the particle dispersion volume added and area of the water surface. These 2-D array films can be transferred onto flat or curved surfaces.

A further preferred aspect of the invention is ultrahigh diffraction efficiency. Ultra strong diffraction efficiencies were obtained from the monolayer of PS particles with a 2-D hexagonal lattice on a thin plastic transparent film on top of a mirror. Without the mirror, the back diffraction is 6-8-fold smaller. The original 2-D array on the Hg surface diffracted over 80% of the incident light back towards the observer, giving rise to a very bright visual signal that reports on the 2-D array spacing. This very bright diffraction results, in part, from the combined diffraction of four beams.

An additional preferred aspect of the invention as described above pertains to particle spacing control and sensors. The lattice spacing of 2-D arrays was able to be controlled so as to control the diffraction wavelength of diffracted light in visible wavelength range. This property was used to design chemical sensors. 580 nm PS 2-D array on polyacrylamide hydrogels containing recognition groups of COOH and crown ether were prepared. These materials were used for sensing pH and lead ions. It was clearly observed that the color changes that occur with changing pH values and $Pb^{2+}$ concentrations that are easily visually observed. In addition, the optical signals from the 2-D arrays are very intense and easily visually monitored. Functional monomers were also utilized, such as acrylic acid, hydroxyethyl methacrylate, N-isopropylacrylamide, even crown ether acrylate for hydrogel fabrication. Preferably, the lattice spacing of 2-D arrays can be controlled by multiple factors, such as pH, temperature, solvent, ion strength, crosslinking density.

While the present disclosure has been described in connection with preferred embodiments thereof, those of ordinary skill in the art will recognize that many modifications and variations are possible. For example, it is contemplated that the highly charged polymeric spheres of the present invention can find useful practical applications in connection with drug delivery and contrast agent diagnostics. In addition to the above, the diffraction efficiencies enable the embedded 2-D arrays to be used for visually attractive paints and coatings, sensors, and as an anti-counterfeiting film.

In the foregoing Detailed Description, various features are grouped together in a single embodiment to streamline the disclosure. This method of disclosure is not to be interpreted as reflecting an intention that the claimed embodiments of the invention require more features than are expressly recited in each claim. The present disclosure is intended to be limited only by the following claims and not by the foregoing description which is intended to set forth the presently preferred embodiments of the invention. Rather, as the following claims reflect, inventive subject matter lies in less than all features of a single disclosed embodiment. Thus, the following claims are hereby incorporated into the Detailed Description, with each claim standing on its own as a separate embodiment.

What is claimed is:

1. A method of sensing a condition, molecule or chemical comprising:
providing a sensor comprising a self-assembled 2-D photonic crystal (PC) array or colloidal crystal array (CCA) of polymeric particles embedded in a matrix comprising a polymer and a recognition agent; wherein the self-assembled 2-D photonic crystal (PC) array or colloidal crystal array (CCA) of polymeric particles was formed by solvent evaporation on a liquid surface; and wherein the recognition agent causes the matrix to swell or shrink in the presence of the condition, molecule or chemical;
exhibiting by the sensor a first light diffraction of a first wavelength in the absence of the condition, molecule or chemical;
exposing the sensor to the condition, molecule or chemical causing the matrix to swell or shrink, thereby altering a spacing of the 2-D PC array or CCA of particles in the matrix such that a second light diffraction from the sensor shows a visually evident color change compared to the first light diffraction.

2. The method of claim 1 wherein the condition, molecule or chemical is pH.

3. The method of claim 1 wherein the recognition agent is selected from the group consisting of carboxylic acid, acrylic acid, urea, uric acid, antigens, antibodies, cations, sodium, potassium, calcium, magnesium, mercury, ammonia, anions, chloride, carbonate, bicarbonate, phosphate and chelating agents, crown ethers, azacrown ethers, borane complexes, calixarene, and cation selective binding proteins.

4. The method of claim 1 wherein the condition, molecule or chemical is lead.

5. The method of claim 1 wherein the polymeric particles comprise polystyrene.

6. The method of claim 1 wherein the liquid comprises water.

7. The method of claim 1 wherein the liquid comprises mercury.

* * * * *